(12) United States Patent
Beld et al.

(10) Patent No.: US 8,735,063 B2
(45) Date of Patent: May 27, 2014

(54) METHODS AND REAGENTS FOR GENOTYPING HCV

(75) Inventors: Marcellinus Beld, Amstelveen (NL); Remko Gouw, Leiden (NL); Toumy Guettouche, Stuttgart (DE); James Hnatyszyn, Coral Gables, FL (US); Carola van der Meer, Amstelhoek (NL)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 204 days.

(21) Appl. No.: 12/609,228

(22) Filed: Oct. 30, 2009

(65) Prior Publication Data
US 2010/0196876 A1    Aug. 5, 2010

Related U.S. Application Data

(63) Continuation of application No. 11/615,789, filed on Dec. 22, 2006, now abandoned.

(60) Provisional application No. 60/753,761, filed on Dec. 23, 2005.

(51) Int. Cl.
| | | |
|---|---|---|
| *C12Q 1/68* | (2006.01) | |
| *C12P 19/34* | (2006.01) | |
| *C07H 21/02* | (2006.01) | |
| *C07H 21/04* | (2006.01) | |

(52) U.S. Cl.
USPC ........ 435/6.11; 435/91.2; 536/23.1; 536/24.3

(58) Field of Classification Search
None
See application file for complete search history.

(56) References Cited

U.S. PATENT DOCUMENTS

2003/0152591 A1    8/2003    Sablon

OTHER PUBLICATIONS

Sandres-Saune, K et al., J. Virol. Meth., vol. 109, pp. 187-193 (2003).*
Laperche, S. et al., J. Clin. Microbiol., vol. 43, pp. 733-739 (Feb. 2005).*
Choo, Q.-L. et al., PNAS USA, vol. 88, pp. 2451-2455 (1991).*
Buck, G.A. et al., Biotechniques, vol. 27, pp. 528-536 (1999).*
Patil, R.V. et al., Nucl. Acids Res., vol. 18, p. 3080 (1990).*
Green, S.M. et al., J. Med. Virol., vol. 45, pp. 197-202 (1995).*
Lu, L. et al., J. Virol., vol. 75, pp. 3004-3009 (2001).*
Morice, Y. et al., J. Gen. Virol., vol. 82, pp. 1001-1012 (2001).*
Qiu, P. et al., BMC Microbiol., vol. 2, No. 29, pp. 1-7 (2002).*
Sandres-Saune et al., Determining hepatitis C genotype by analyzing the sequence of the NS5b region, J. of Virol. Methods, 109(2): 187-193 (2003).
Murphy et al., Use of nucleotide sequence analysis of the NS5B region for routine genotyping of hepatitis C virus: identification of numerous variants not classifiable into the known HCV genotyopes, Hepatology, 38(4, supp. 1): 423A (2003).
GenBank Accession No. D01217 (gi: 221604; Nov. 1992).
Tokita et al., Hepatitis C virus from Jakarta, Indonesia classifiable into novel genotypes in the second (2e and 2f), tenth (10a) and eleventh (11a), genetic groups, J. General Virology, vol. 77:293-301 (1996).

* cited by examiner

*Primary Examiner* — Teresa E Strzelecka

(57) ABSTRACT

The present invention is directed to methods and reagents for determining the genotype of a hepatitis C virus (HCV) species present in a test sample. The invention more particularly relates to mixtures of degenerate amplification and sequencing primers, and methods of using such primers, that are complementary to a plurality of HCV species, and are capable of generating nucleotide sequence information for a region of NS5B of HCV that is, for each species, indicative of the type and/or subtype, of the species present in the sample.

6 Claims, 3 Drawing Sheets

FIG. 2A

```
1a.US.HCV-H_M67463        Primers for NS5b full gene                    Locations 7473   CCC GAC TCC GAC GTT GAG TCC TAT TCT TCC ATG CCC CCC CTG GAG   7517      NS5A 7518   GGG GAG CCT GGG GAT CCG GAT CTC AGC GAC GGG TCA TGG TCG ACG   7562
                                                                           ┌────────────── Start NS5b-gene
7563   GTC AGT AGT GGG GCC GAC ACG GAA GAT GTC GTG TGC TGC│TCA ATG   7607         7602

7608   TCT TAT TCC TGG ACA GGC GCA CTC GTC ACC CCG TGC GCT GCG GAG   7652

7653   GAA CAA AAA CTG CCC ATC AAC GCA CTG AGC AAC TCG TTG CTA CGC   7697

7698   CAT CAC AAT CTG GTG TAT TCC ACC ACT TCA CGC AGT GCT TGC CAA   7742

7743   AGG AAG AAG AAA GTC ACA TTT GAC AGA CTG CAA GTT CTG GAC AGC   7787

7788   CAT TAC CAG GAC GTG CTC AAG GAG GTC AAA GCA GCG GCG TCA AAA   7832

7833   GTG AAG GCT AAC TTG CTA TCC GTA GAG GAA GCT TGC AGC CTG ACG   7877

7878   CCC CCA CAT TCA GCC AAA TCC AAG TTT GGC TAT GGG GCA AAA GAC   7922

7923   GTC CGT TGC CAT GCC AGA AAG GCC GTA GCC CAC ATC AAC TCC GTG   7967

7968   TGG AAA GAC CTT CTG GAA GAC AGT GTA ACA CCA ATA GAC ACT ACC   8017

8013   ATC ATG GCC AAG AAC GAG GTT TTC TGC GTT CAG CCT GAG AAG GGG   8057

8058   GGT CGT AAG CCA GCT CGT CTC ATC GTG TTC CCC GAC CTG GGC GTG   8102

8103   CGC GTG TGC GAG AAG ATG GCC CTG TAC GAC GTG GTT AGC AAG CTC   8147

8148   CCC TTG GCC GTG ATG GGA AGC TCC TAC GGA TTC CAA TAC TCA CCA   8192

8193   GGA CAG CGG GTT GAA TTC CTC GTG CAA GCG TGG AAG TCC AAG AAG   8237

8238   ACC CCG ATG GGG CTC TCG TAT GAT ACC CGC TGT TTT GAC TCC ACA   8282      M-NS5b-FF1+FF2
                                                                              M-NS5bSeq-Cy5.5
8283   GTC ACT GAG AGC GAC ATC CGT ACG GAG GAG GCA ATT TAC CAA TGT   8327

8328   TGT GAC CTG GAC CCC CAA GCC CGC GTG GCC ATC AAG TCC CTC ACT   8372
                                                                              GeneLibrary
8373   GAG AGG CTT TAT GTT GGG GGC CCT CTT ACT AAT TCA AGG GGG GAA   8417

8418   AAC TGC GGC TAC CGC AGG TGC CGC GCG AGC AGA GTA CTG ACA ACT   8462

8463   AGC TGT GGT AAC ACC CTC ACT CGC TAC ATC AAG GCC CGG GCA GCC   8507

8508   TGT CGA GCC GCA GGG CTC CAG GAC TGC ACC ATG CTC GTG TGT GGC   8552

8553   GAC GAC TTA GTC GTT ATC TGT GAA AGT GCG GGG GTC CAG GAG GAC   8597

8598   GCG GCG AGC CTG AGA GCC TTC ACG GAG GCT ATG ACC AGG TAC TCC   8642      M-NS5b-RR1
                                                                              M-NS5bSeq-Cy5
8643   GCC CCC CCC GGG GAC CCC CCA CAA CCA GAA TAC GAC TTG GAG CTT   8687

8688   ATA ACA TCA TGC TCC TCC AAC GTG TCA GTC GCC CAC GAC GGC GCT   8732
```

FIG. 2B

```
8733  GGA AAG AGG GTC TAC TAC CTT ACC CGT GAC CCT ACA ACC CCC CTC  8777
8778  GCG AGA GCC GCG TGG GAG ACA GCA AGA CAC ACT CCA GTC AAT TCC  8822
8823  TGG CTA GGC AAC ATA ATC ATG TTT GCC CCC ACA CTG TGG GCG AGG  8867
8868  ATG ATA CTG ATG ACC CAC TTC TTT AGC GTC CTC ATA GCC AGG GAT  8912
8913  CAG CTT GAA CAG GCT CTC AAC TGC GAG ATC TAC GGA GCC TGC TAC  8957
8958  TCC ATA GAA CCA CTG GAT CTA CCT CCA ATC ATT CAA AGA CTC CAT  9002
9003  GGC CTC AGC GCA TTT TCA CTC CAC AGT TAC TCT CCA GGT GAA ATT  9047
9048  AAT AGG GTG GCC GCA TGC CTC AGA AAA CTT GGG GTC CCG CCC TTG  9092
9093  CGA GCT TGG AGA CAC CGG GCC TGG AGC GTC CGC GCT AGG CTT CTG  9137
9138  GCC AGA GGA GGC AAG GCT GCC ATA TGT GGC AAG TAC CTC TTC AAC  9182
9183  TGG GCA GTA AGA ACA AAG CTC AAA CTC ACT CCG ATA ACG GCC GCT  9227
9228  GGC CGG CTG GAC TTG TCC GGC TGG TTC ACG GCT GGC TAC AGC GGG  9272
9273  GGA GAC ATT TAT CAC AGC GTG TCT CAT GCC CGG CCC CGC TGG TTC  9317
9318  TGG TTT TGC CTA CTC CTG CTT GCT GCA GGG GTA GGC ATC TAC CTC  9362
9363  CTC CCC AAC CGA TGA AGA TTG GGC TAA CCA CTC AGG CCA ATA GG    9407
9408  CCA TTC CCT  9416
```
End of NS5b-gene

US 8,735,063 B2

METHODS AND REAGENTS FOR GENOTYPING HCV

CROSS REFERENCE TO RELATED APPLICATION

This application is a continuation of U.S. patent application Ser. No. 11/615,789, now abandoned, filed Dec. 22, 2006, which claims priority to U.S. Provisional Patent Application No. 60/753,761, filed Dec. 23, 2005, the disclosures of which are hereby incorporated in their entirety by this reference.

TECHNICAL FIELD OF THE INVENTION

The present invention is generally directed to methods and materials for genotyping a hepatitis C virus (HCV) species found in a test sample.

BACKGROUND OF THE INVENTION

Hepatitis C virus (HCV) is estimated to infect at approximately 170 million people worldwide, and is responsible for chronic liver disease and increased risk of cirrhosis and hepatocellular carcinoma. Treatment of HCV is principally limited to antiviral regimens, the efficacies of which are largely influenced by several biological parameters, such as the virus genotype. HCV genotyping has therefore been widely used to predict the response to antiviral therapy and to optimize the duration of treatment. HCV genotyping has also become an essential tool for epidemiological studies and for tracing sources of contamination by HCV.

The plus-strand HCV RNA genome is approximately 9600 nucleotides in length and encodes at least one open-reading frame with approximately 3010 amino acids. In infected cells, this polyprotein is cleaved at multiple sites by cellular and viral proteases to produce structural and non-structural (NS) proteins. HCV isolates are characterized by a high degree of genetic variability due to the lack of fidelity of the HCV RNA-dependent RNA polymerase, which is encoded by the non-structural 5B (NS5B) gene. In addition, as a result of endogenous mutation or infection by a plurality of species, also gives rise to genetically variable quasi-species of HCV within a single patient. Six main genotypes of HCV, and over a hundred subtypes, have been described.

The genetic variability of HCV complicates the processes of amplification, sequencing, and genotyping. These processes typically rely upon use of oligonucleotide primers and probes (e.g., PCR amplification primers, sequencing primers, and site-specific probes) that are complementary to and are capable of hybridizing to corresponding nucleic acid sequences of the HCV genome. As a result of the high degree of variability of the HCV genome, oligonucleotide primers and probes complementary to one species of HCV may not be complementary to another species. Such primers and probes must therefore be designed for specificity to highly conserved regions. Alternatively, assays must use mixtures of degenerate primers and probes that are complementary to all species.

Some genotyping methods have focused on the 5' noncoding (5'NC) region. The 5' non-coding (NC) region of HCV is highly conserved, yet contains type-specific polymorphisms that can be utilized to distinguish between genotypes. To date, most of the commercially available 5'NC region genotyping assays have been based on PCR amplification and fragment analysis by RFLP or hybridization to oligonucleotide probes. These types of assay are rapid but not as accurate as sequencing-based assays. For this reason, alternative genomic regions have been proposed for use in genotyping HCV, including the NS5B region.

The most accurate and direct method of genotyping HCV is to sequence the virus genome in a region that is sufficiently divergent among various species to distinguish between virus types and subtypes. Equally importantly, databases for phylogenetic analysis must be readily available to analyze the sequences generated from these regions.

Commercially available sequencing-based HCV genotyping assays include, for example, the TRUGENE HCV 5'NC Genotyping Kit (Bayer HealthCare), which is a rapid sequencing-based assay utilizing the 5'NC region of HCV. Sequence data generated by this assay are directly analyzed utilizing a phylogenetic 5'NC region database (TRUGENE HCV 5'NC software module v3.1.1). Previously, 5'NC databases have included sequences from various sources that have never been fully validated and, in some cases, subtype assignments for particular strains have been discordant when 5'NC or NS5B sequences were analyzed.

There is a continuing need to improve sequencing-based HCV assays, so as to improve identification of HCV types and subtypes for purposes of clinical analysis and therapeutic intervention.

SUMMARY OF THE INVENTION

The present invention is generally directed to methods and reagents for genotyping a hepatitis C virus (HCV) species found in a test sample. More particularly, the present invention is directed to an improved method of amplifying and sequencing a portion of the NS5B region of an HCV species in a sample and determining its genotype.

One aspect of the invention relates to a method for determining the genotype of a hepatitis C virus (HCV) species present in a test sample by sequencing at least a portion of the NS5B region of HCV that, for each of a plurality of HCV species, is indicative of the type and/or subtype of that species.

In one embodiment, the method comprises (a) determining the nucleotide sequence of at least a portion of the NS5b region of HCV indicative of the genotype of said HCV species present in the test sample, wherein the corresponding nucleotide sequence of a plurality of HCV species is indicative of a distinct genotype of that HCV species; and (b) correlating the nucleotide sequence of said portion of the NS5b region determined in (a) with the genotype of one of said plurality of HCV species.

In another embodiment, the method comprises (a) determining the nucleotide sequence of at least a portion of the NS5b region of HCV indicative of the genotype of said HCV species present in the test sample, wherein the corresponding nucleotide sequence of each of a plurality of HCV species having HCV genotypes 1, 2, 3, 4, 5, and 6 is indicative of a distinct genotype of that HCV species; and (b) correlating the nucleotide sequence of said portion of the NS5b region determined in (a) with one of said HCV genotypes 1, 2, 3, 4, 5 and 6.

In yet another embodiment, the method comprises (a) determining the nucleotide sequence of at least a portion of the NS5b region of HCV indicative of the genotype and subtype of said HCV species present in the test sample, wherein the corresponding nucleotide sequence of each HCV species having HCV genotypes 1, 2, 3, 4, 5, and 6, and each of the HCV subtypes set forth in Table 1, is indicative of a distinct genotype and subtype of that HCV species; and (b) correlating the nucleotide sequence of said portion of the NS5b region determined in (a) with one of said HCV genotypes 1, 2, 3, 4, 5 and 6 and one of said HCV subtypes set forth in Table 1.

In one particular embodiment of the above methods, the portion of the NS5b region of HCV consists essentially of the region from about nucleotide position 8344 to about 8547 shown in FIG. 2.

In another particular embodiment of the above methods, the portion of the NS5b region of HCV consists essentially of the region from nucleotide position 8344 to 8547 shown in FIG. 2.

In another embodiment, the method of present invention comprises (a) providing a mixture of degenerate oligonucleotide sequencing primers capable of generating nucleotide sequence of at least a portion of the NS5b region of a plurality of HCV species present in a test sample, wherein the corresponding nucleotide sequence of each of said plurality of HCV species is indicative of a distinct genotype of that HCV species; (b) determining the nucleotide sequence of said portion of the NS5b region indicative of the genotype of said HCV species present in the test sample; and (c) correlating the nucleotide sequence of said portion of the NS5b region of said HCV species determined in (b) with a genotype of one of said plurality of HCV species.

In yet another embodiment, the method comprises (a) providing a mixture of degenerate oligonucleotide sequencing primers capable of generating nucleotide sequence of at least a portion of the NS5b region of a plurality of HCV species, wherein the corresponding nucleotide sequence of each of said plurality of HCV species is indicative of one of HCV genotypes 1, 2, 3, 4, 5 and 6; (b) determining the nucleotide sequence of said portion of the NS5b region indicative of the genotype of said HCV species present in the test sample; and (c) correlating the nucleotide sequence of said portion of the NS5b region of said HCV species determined in (b) with one of HCV genotypes 1, 2, 3, 4, 5 and 6.

In still another embodiment, the method comprises (a) providing a mixture of degenerate oligonucleotide sequencing primers capable of generating nucleotide sequence of at least a portion of the NS5b region of a plurality of HCV species, wherein the corresponding nucleotide sequence of each of said plurality of HCV species is indicative of one of HCV genotypes 1, 2, 3, 4, 5 and 6 and one of the subtypes set forth in Table 1; (b) determining the nucleotide sequence of said portion of the NS5b region indicative of the genotype and subtype of said HCV species present in the test sample; and (c) correlating the nucleotide sequence of said portion of the NS5b region of said HCV species determined in (b) with an HCV genotype and subtype (for example, one of HCV genotypes 1, 2, 3, 4, 5 and 6 and one of the subtypes set forth in Table 1).

In one particular embodiment, the mixture of degenerate oligonucleotide sequencing primers comprises degenerate nucleotide sequences complementary to the NS5b region of a plurality of HCV species from about nucleotide 8256 to about 8278 [CLIP sequencing primer M-NS5b-Cy5.5] shown in FIG. 2, or its complement, and degenerate nucleotide sequences complementary to the NS5b region of a plurality of HCV species from about nucleotide 8611 to about 8633 (for example, CLIP sequencing primer M-NS5b-Cy5) shown in FIG. 2, or its complement.

In another particular embodiment, the mixture of degenerate oligonucleotide sequencing primers comprises degenerate nucleotide sequences complementary to the NS5b region of a plurality of HCV species from nucleotide 8256 to 8278 (for example, CLIP sequencing primer M-NS5b-Cy5.5) shown in FIG. 2, or its complement, and degenerate nucleotide sequences complementary to the NS5b region of a plurality of HCV species from nucleotide 8611 to 8633 (for example, CLIP sequencing primer M-NS5b-Cy5) shown in FIG. 2, or its complement.

In yet another particular embodiment, the mixture of degenerate oligonucleotide sequencing primers comprise degenerate oligonucleotide sequences defined by one or more of the following formulas, or complements thereof:

```
SEQ ID NO: 1: 5'-TAT GAY ACC CGC TGY TTY GAY
TC-3';
and

SEQ ID NO: 2: 5'-VGT CAT RGC ITC YGT RAA GGC
TC-3'.
```

Another aspect of the invention relates to a method for determining the genotype of a hepatitis C virus (HCV) species present in a test sample by amplifying at least a portion of the NS5B region of HCV that, for each of a plurality of HCV species, is indicative of the type and/or subtype of that species.

In one embodiment, the method comprises (a) providing a mixture of degenerate oligonucleotide PCR primers comprising degenerate nucleotide sequences complementary to the NS5b region of a plurality of HCV species from about nucleotide 8245 to about 8269 (for example, forward primers FF1 and/or FF2) shown in FIG. 2, or its complement; and degenerate nucleotide sequences complementary to the NS5b region of a plurality of HCV species from about nucleotide 8616 to about 8641 (for example, reverse primers RR1) shown in FIG. 2, or its complement, and (b) amplifying the nucleotide sequence of said portion of the NS5b region.

In a particular embodiment, the mixture of degenerate oligonucleotide PCR primers comprises degenerate nucleotide sequences complementary to the NS5b region of a plurality of HCV species from nucleotide 8256 to 8278 (for example, CLIP sequencing primers M-NS5b-Cy5.5) shown in FIG. 2, or its complement; and degenerate nucleotide sequences complementary to the NS5b region of a plurality of HCV species from nucleotide 8611 to 8633 (for example, CLIP sequencing primers M-NS5b-Cy5) shown in FIG. 2, or its complement.

In another particular embodiment, the mixture of degenerate oligonucleotide PCR primers comprise degenerate oligonucleotide sequences defined by one or more of the following formulas, or complements thereof:

```
SEQ ID NO: 6: 5'-TGG SBT TYK CNT AYG AYA CYM GNT
G-3'

SEQ ID NO: 9: 5'-GAR TAY CTV GTC ATR GCI TCY GTR
AA-3'
```

In yet another particular embodiment, the mixture of degenerate oligonucleotide PCR primers comprise degenerate oligonucleotide sequences defined by one or more of the following formulas, or complements thereof:

```
SEQ ID NO: 3: 5'-TGG GGT TCK CGT ATG AYA CCC GCT
G-3'

SEQ ID NO: 4: 5'-TGG GGT TCK CIT ATG AYA CYM GIT
G-3'

SEQ ID NO: 9: 5'-GAR TAY CTV GTC ATR GCI TCY GTR
AA-3'
```

BRIEF DESCRIPTION OF THE DRAWINGS

FIG. 2 shows the nucleotide sequence of NS5b domain of HCV, as set forth in GenBank Accession No. M67463. Primer regions are highlighted and designated in the margins. FIG. 2 corresponds to SEQ ID NO:12.

DETAILED DESCRIPTION OF THE INVENTION

Definitions

Figure 1:
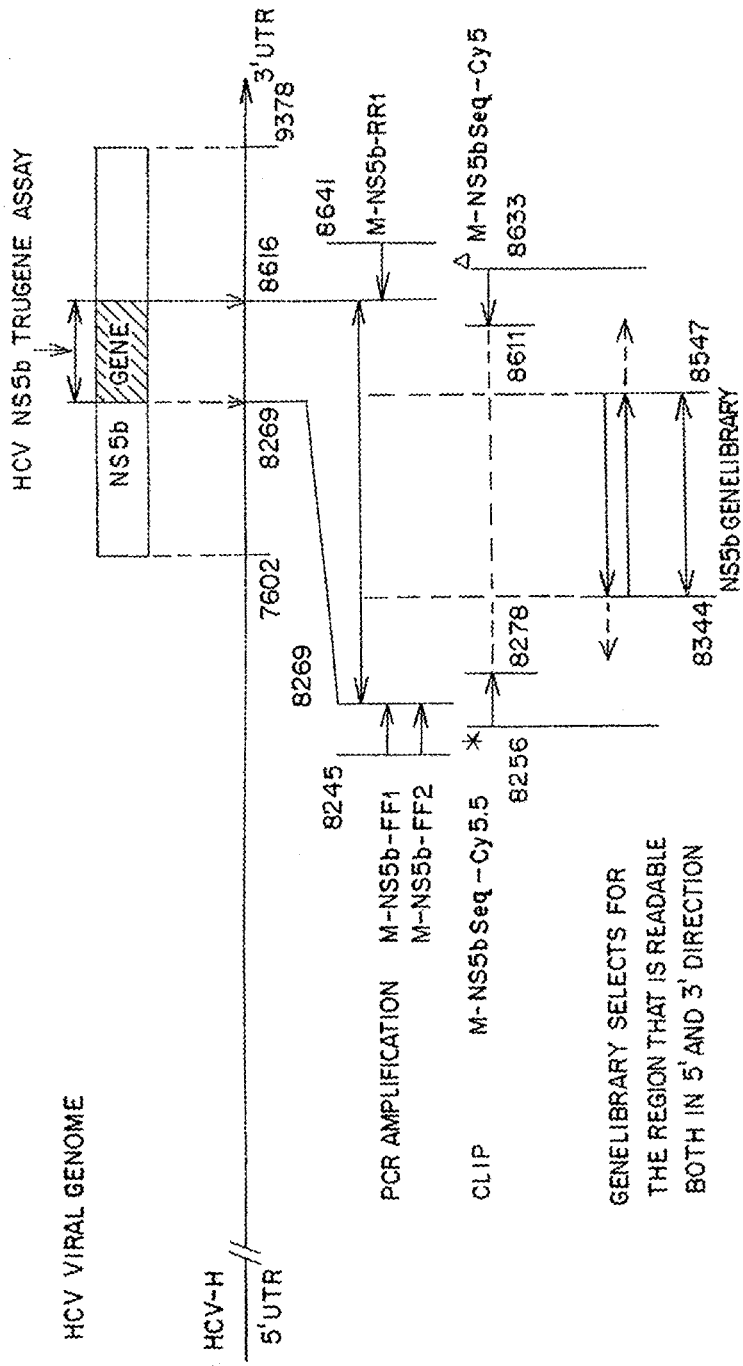
FIG. 1 is a schematic diagram showing the HCV NS5b domain and relevant regions utilized in particular embodiments of the invention.

While the terminology used in this application is standard within the art, the following definitions of certain terms are provided to assure clarity.

Units, prefixes, and symbols may be denoted in their SI accepted form. Unless otherwise indicated, nucleic acids are written left to right in 5' to 3' orientation. Numeric ranges recited herein are inclusive of the numbers defining the range and include and are supportive of each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. In the case of any amino acid or nucleic sequence discrepancy within the application, the figures control.

As used herein, the term "amplification" means the process of increasing the relative abundance of one or more specific genes or gene fragments in a reaction mixture with respect to other genes.

The term "consisting essentially of" means, when used herein in reference to specified nucleotide sequences, the specified sequence and any additional sequence that does not materially affect the complementarity of the sequence and ability of the sequence to hybridize to a plurality of HCV types or subtypes.

As used herein, a "sample" refers to any substance containing or suspected of containing a nucleic acid, such as RNA or DNA, and includes samples of tissue or fluid isolated from an individual or individuals, including but not limited to, for example, skin, plasma, serum, spinal fluid, lymph fluid, synovial fluid, urine, tears, blood cells, organs, tumors, and also to samples of in vitro cell culture constituents (including but not limited to conditioned medium resulting from the growth of cells in cell culture medium, recombinant cells and cell components).

The term "nucleotide" means the nucleotides adenosine, cytosine, guanine and thymine are represented by their one-letter codes A, C, G, and T respectively. In representations of degenerate primers, the symbol R refers to either G or A, the symbol Y refers to either T/U or C, the symbol M refers to either A or C, the symbol K refers to either G or T/U, the symbol S refers to G or C, the symbol W refers to either A or T/U, the symbol B refers to "not A", the symbol D refers to "not C", the symbol H refers to "not G", the symbol V refers to "not T/U" and the symbol N refers to any nucleotide. The symbol 1 represents inosine, which is a neutral base that generally will pair with any C, T or A. In the specification and claims of this application, a degenerate primer refers to any or all of the combinations of base choices and to either DNA or the corresponding RNA sequence (i.e., with T replaced by U). Thus, a degenerate primer may represent a single species, or a mixture of two species which fall within the choices, or a mixture of three choices which fall with the choices, and so on up to a mixture containing all the possible combinations.

The terms "nucleic acid", "polynucleotide" and "oligonucleotide" refer to primers, probes, oligomer fragments to be detected, oligomer controls and unlabeled blocking oligomers and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA. The oligonucleotide is comprised of a sequence of approximately at least 6 nucleotides, preferably at least about 10-12 nucleotides, and more preferably at least about 15-25 nucleotides corresponding to a region of the designated nucleotide sequence. The term "corresponding to," as used herein, as used herein to define a nucleic acid sequence in terms of a reference nucleotide sequence, means nucleotide sequences that match all or part of the reference sequence, and nucleotide sequences that are the complement of all or part of the reference sequence.

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature; and (3) is not found in nature.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature.

The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primer and use of the method. For example, depending on the complexity of the target sequence, the oligonucleotide primer typically contains 15-25 nucleotides, although it may contain more or fewer nucleotides. Short primer molecules generally require lower temperatures to form sufficiently stable hybrid complexes with the template.

The term "extension primer" means a polynucleotide sequence that is complementary to a template sequence, and which is capable of hybridizing and extending a sequence under polymerase chain reaction conditions.

The term "complement" and its related adjectival form "complementary," when used in reference to two nucleic acid sequences, means that when two nucleic acid sequences are aligned in anti-parallel association (with the 5' end of one sequence paired with the 3' end of the other sequence) the corresponding G and C nucleotide bases of the sequences are paired, and the corresponding A and T nucleotide bases are paired. Certain bases not commonly found in natural nucleic acids may be included in the nucleic acids of the present invention and include, for example, inosine and 7-deazaguanine.

The term "location" or "position" of a nucleotide in a genetic locus means the number assigned to the nucleotide in the gene, generally taken from the CDNA sequence of the genomic sequence of a gene.

The term "oligonucleotide primer" means a molecule comprised of more than three deoxyribonucleotides or ribonucleotides. Its exact length will depend on many factors relating to the ultimate function and use of the oligonucleotide primer, including temperature of the annealing reaction, and the source and composition of the primer. Amplification primers must be sufficiently long to prime the synthesis of extension products in the presence of the agent for polymerization. The oligonucleotide primer is capable of acting as an initiation point for synthesis when placed under conditions which induce synthesis of a primer extension product complementary to a nucleic acid strand. The conditions can include the presence of nucleotides and an inducing agent such as a DNA polymerase at a suitable temperature and pH. In preferred embodiments, the primer is a single-stranded oligodeoxyribonucleotide of sufficient length to prime the synthesis of an extension product from a specific sequence in the presence of an inducing agent. In one aspect of the present invention, the oligonucleotide primers are from about 15 to about 30 nucleotides long, although a primer may contain more or fewer nucleotides. The oligonucleotide primers are preferably at least 15, 16, 17, 18, 19 or 20 nucleotides long. More preferably, primers will contain around 20-25 nucleotides. Sensitivity and specificity of the oligonucleotide primers are determined by the primer length and uniqueness of sequence within a given sample of template nucleic acid. Primers which are too short, for example, may show non-specific binding to a wide variety of sequences.

The practice of the present invention will employ, unless otherwise indicated, conventional techniques of molecular biology, microbiology, recombinant DNA techniques, oligonucleotide synthesis which are within the skill of the art. Such techniques are explained fully in the literature. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)); Oligonucleotide Synthesis (M. J. Gait, ed., 1984); Nucleic Acid Hybridization (B. D. Hames & S. J. Higgins, eds., 1984); A Practical Guide to Molecular Cloning (B. Perbal, 1984); and a series, Methods in Enzymology (Academic Press, Inc.), the contents of all of which are incorporated herein by reference.

The term "reverse transcription" means the process of generating a DNA complement to an RNA molecule, and is generally accomplished with the use of a reverse transcriptase enzyme. A primer may be used to initiate polymerization; this primer may be one of a primer pair later used for PCR amplification. The RNA molecule is then separated from the copied DNA ("cDNA") or degraded by an RNAse H activity of an enzyme thus allowing the second strand of cDNA to be generated by a template dependent DNA polymerase. This method is disclosed in Units 3.7 and 15.4 of Current Protocols in Molecular Biology, Eds. Ausubel, F. M. et al, (John Wiley & Sons; 1995), the contents of which are incorporated herein by reference.

The term "sequencing" means the determination of the order of nucleotides in at least a part of a gene.

The practice of the present invention will employ, unless otherwise indicated, conventional techniques of molecular biology, microbiology, recombinant DNA techniques, oligonucleotide synthesis which are within the skill of the art. Such techniques are explained fully in the literature. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)); Oligonucleotide Synthesis (M. J. Gait, ed., 1984); Nucleic Acid Hybridization (B. D. Hames & S. J. Higgins, eds., 1984); A Practical Guide to Molecular Cloning (B. Perbal, 1984); and a series, Methods in Enzymology (Academic Press, Inc.), the contents of all of which are incorporated herein by reference.

Source of DNA

In one aspect of the invention, the method comprises first obtaining from the patient sample a double-stranded polynucleotide template encompassing the mutation of interest. The double-stranded polynucleotide template may initially comprise genomic DNA, a fragment of genomic DNA, or cDNA reverse transcribed from RNA. This template will encompass not only the mutation of interest, but may also encompass the region containing the length polymorphism giving rise to multiple quasispecies.

A double-stranded polynucleotide template will typically be prepared from a patient sample by treating a patient sample containing DNA so as to make all or a portion of the DNA in the sample accessible for hybridization with oligonucleotide primers, for example by lysis, centrifugation to remove cellular debris and proteolytic digestion to expose the DNA. The DNA template may therefore contain only nuclear DNA, only mitochondrial DNA, or some sub-fraction of nuclear or mitochondrial DNA obtained by isolation from a tissue sample. The DNA template may also be prepared by conversion, for example by reverse transcription, of a total mRNA preparation or the genome of an RNA virus to cDNA; DNA isolated from an individual bacterial colony growing on a plate or from an enriched bacterial culture; and a viral DNA preparation where substantially the entire viral genome is isolated.

DNA can be prepared from fluid samples, e.g., blood or urine or tissue samples by any of a number of techniques, including lysis, centrifugation to remove cellular debris and proteolytic digestion to expose the DNA; salt precipitation or standard SDS-proteinase K-phenol extraction. Samples can also be prepared using kits, for example the Pure Gene DNA Isolation Kit (Gentra).

Amplification of Nucleic Acids

The present invention includes methods and reagents for amplification of DNA to provide an abundant source of DNA for subsequent sequencing.

Typically, prior to sequencing, a sequencing template is prepared by first amplifying a region of DNA that encompasses the target region to be sequenced. It is not necessary that the sequence to be amplified be present initially in a pure form; it may be a minor fraction of a complex mixture or a portion of nucleic acid sequence. The starting nucleic acid may contain more than one desired specific nucleic acid sequence which may be the same or different. Therefore, the present process is useful not only for producing large amounts of one specific nucleic acid sequence, but also for amplifying simultaneously more than one different specific nucleic acid sequence located on the same or different nucleic acid molecules if more than one of the base pair variations in sequence is present.

The present invention is directed to methods and reagents, including amplification and sequencing primers, used for genotyping HCV. The present invention utilizes well-known methods for amplifying specific nucleic acid sequences using the technique of polymerase chain reaction (or PCR) or some other primer extension-based methodology. Polymerase chain reaction (PCR) methods are very widely known in the art. Such methods are described, for example, in U.S. Pat. Nos. 4,683,195, 4,683,202, and 4,800,159; K. Mullis, Cold Spring Harbor Symp. Quant. Biol., 51:263-273 (1986); and C. R. Newton & A. Graham, Introduction to Biotechniques: PCR, 2.sup.nd Ed., Springer-Verlag (New York: 1997), the disclosures of which are incorporated herein by reference. PCR involves the use of pairs of primers, one for each complementary strand of the duplex DNA (wherein the coding strand is referred to as the "sense strand" and its complementary strand is referred to as the "anti-sense strand), that will hybridize at sites located on either side of a region of interest in a gene. Chain extension polymerization is then carried out in repetitive cycles to increase the number of copies of the region of interest exponentially. To briefly summarize, in the first step of the PCR reaction, the nucleic acid molecules of the sample are transiently heated, and then cooled, in order to denature double stranded molecules. Forward and reverse primers are present in the amplification reaction mixture at an excess concentration relative to the sample target. When the sample is incubated under conditions conducive to hybridization and polymerization, the primers hybridize to the complementary strand of the nucleic acid molecule at a position 3' to the sequence of the region desired to be amplified that is the complement of the sequence whose amplification is desired. Upon hybridization, the 3' ends of the primers are extended by the polymerase. The extension of the primer results in the synthesis of a DNA molecule having the exact sequence of the complement of the desired nucleic acid sample target. The PCR reaction is capable of exponentially amplifying the desired nucleic acid sequences, with a near doubling of the number of molecules having the desired sequence in each cycle. Thus, by permitting cycles of hybridization, polymerization, and denaturation, an exponential increase in the concentration of the desired nucleic acid molecule can be achieved. The amplified polynucleotide may be used as the template for a sequencing reaction. Gelfand et al. have described a thermostable enzyme, "Taq polymerase", derived from the organism *Thermus aquaticus*, which is useful in this amplification process (see U.S. Pat. Nos. 4,889,818; 5,352,600; and 5,079,352 which are incorporated herein by reference). Alternative amplification techniques such as NASBA, 3SR, Qb Replicase, and Branched Chain Amplification are known and available to persons skilled in the art. The term "RT-PCR" refers generally to amplification which includes a reverse transcription step to permit amplification of RNA sequences.

Preparation of Polynucleotide Amplification Templates

The present invention relates to amplification and sequencing of HCV and its variant forms. The method of the present invention may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid.

It is not necessary that the sequence to be amplified be present initially in a pure form; it may be a minor fraction of a complex mixture or a portion of nucleic acid sequence. The starting nucleic acid may contain more than one desired specific nucleic acid sequence which may be the same or different. Therefore, the present process is useful not only for producing large amounts of one specific nucleic acid sequence, but also for amplifying simultaneously more than one different specific nucleic acid sequence located on the same or different nucleic acid molecules if more than one of the base pair variations in sequence is present.

The nucleic acid templates may be obtained from any source, for example, from plasmids such as pBR322, from cloned DNA or RNA, or from natural DNA or RNA from any source. DNA or RNA may be extracted from blood, tissue material or amniotic cells by a variety of techniques such as that described by Maniatis et al., Molecular Cloning (1982), 280-281.

The cells may be directly used without purification of the nucleic acid if they are suspended in hypotonic buffer and heated to about 90°-100° C., until cell lysis and dispersion of intracellular components occur, generally about 1 to 15 minutes. After the heating step the amplification reagents may be added directly to the lysed cells. This direct cell detection method may be used on peripheral blood lymphocytes and amniocytes.

The target nucleic acid contained in the sample will initially be in the form of RNA, and is preferably reverse transcribed into cDNA, and then denatured, using any suitable denaturing method, including physical, chemical, or enzymatic means, which are known to those of skill in the art. A preferred physical means for strand separation involves heating the nucleic acid until it is completely (>99%) denatured. Typical heat denaturation involves temperatures ranging from about 80° C. to about 105° C., for times ranging from a few seconds to minutes. As an alternative to denaturation, the target nucleic acid may exist in a single-stranded form in the sample, such as, for example, single-stranded RNA or DNA viruses.

The denatured nucleic acid strands are then incubated with preselected oligonucleotide primers, and, optionally, a labeled oligonucleotide (referred to herein as a "probe") for purposes of detecting the amplified sequence) under conditions that facilitate the binding of the primers and probes to the single nucleic acid strands. As known in the art, the primers are selected so that their relative positions along a duplex sequence are such that an extension product synthesized from one primer, when the extension product is separated from its template (complement), serves as a template for the extension of the other primer to yield a replicate chain of defined length.

Amplification of HCV

One aspect of the present invention relates to a method for determining the genotype of a hepatitis C virus (HCV) species present in a test sample by amplifying at least a portion of the NS5B region of HCV that, for each of a plurality of HCV species, is indicative of the type and/or subtype of that species.

In one embodiment, the method comprises (a) providing a mixture of degenerate oligonucleotide PCR primers comprising degenerate nucleotide sequences complementary to the NS5b region of a plurality of HCV species from about nucleotide 8245 to about 8269 (for example, forward primers FF1 and/or FF2) shown in FIG. 2, or its complement; and degenerate nucleotide sequences complementary to the NS5b region of a plurality of HCV species from about nucleotide 8616 to about 8641 (for example, reverse primers RR1) shown in FIG. 2, or its complement; and (b) amplifying the nucleotide sequence of said portion of the NS5b region.

In a particular embodiment, the mixture of degenerate oligonucleotide PCR primers comprises degenerate nucleotide sequences complementary to the NS5b region of a plurality of HCV species from nucleotide 8256 to 8278 (for example, CLIP sequencing primers M-NS5b-Cy5.5) shown in FIG. 2, or its complement; and degenerate nucleotide sequences complementary to the NS5b region of a plurality of HCV species from nucleotide 8611 to 8633 (for example, CLIP sequencing primers M-NS5b-Cy5) shown in FIG. 2, or its complement.

In another particular embodiment, the mixture of degenerate oligonucleotide PCR primers comprise degenerate oligonucleotide sequences defined by one or more of the following formulas, or complements thereof:

SEQ ID NO: 6: 5'-TGG SBT TYK CNT AYG AYA CYM GNT G-3'

SEQ ID NO: 9: 5'-GAR TAY CTV GTC ATR GCI TCY GTR AA-3'

In yet another particular embodiment, the mixture of degenerate oligonucleotide PCR primers comprise degenerate oligonucleotide sequences defined by one or more of the following formulas, or complements thereof:

SEQ ID NO: 3: 5'-TGG GGT TCK CGT ATG AYA CCC GCT G-3'

SEQ ID NO: 4: 5'-TGG GGT TCK CIT ATG AYA CYM GIT G-3'

SEQ ID NO: 9: 5'-GAR TAY CTV GTC ATR GCI TCY GTR AA-3'

Sequencing of Nucleic Acids

Amplification of DNA as described above will result in an abundant source of DNA for sequencing. The polynucleotide templates prepared as described above are sequenced using any of the numerous methods available and known to those in the art for sequencing nucleotides.

Numerous methods are available and known to those in the art for sequencing nucleotides, any of which may be used in the method of the present invention. One well known method of sequencing is the "chain termination" method first described by Sanger et al., PNAS (USA) 74(12): 5463-5467 (1977) and detailed in Sequenase® 2.0 product literature (Amersham Life Sciences, Cleveland) and more recently elaborated in European Patent EP-B1-655506, the content of which are all incorporated herein by reference. In this process, DNA to be sequenced is isolated, rendered single stranded, and placed into four vessels. In each vessel are the necessary components to replicate the DNA strand, which include a template-dependent DNA polymerase, a short primer molecule complementary to the initiation site of sequencing of the DNA to be sequenced and deoxyribonucleotide triphosphates for each of the bases A, C, G and T, in a buffer conducive to hybridization between the primer and the DNA to be sequenced and chain extension of the hybridized primer. In addition, each vessel contains a small quantity of one type of dideoxynucleotide triphosphate, e.g. dideoxyadenosine triphosphate ("ddA"), dideoxyguanosine triphosphate ("ddG"), dideoxycytosine triphosphate ("ddC"), dideoxythymidine triphosphate ("ddT"). In each vessel, each piece of the isolated DNA is hybridized with a primer. The primers are then extended, one base at a time to form a new nucleic acid polymer complementary to the template DNA. When a dideoxynucleotide is incorporated into the extending polymer, the polymer is prevented from further extension. Accordingly, in each vessel, a set of extended polymers of specific lengths are formed which are indicative of the positions of the nucleotide corresponding to the dideoxynucleotide in that vessel. These sets of polymers are then evaluated using gel electrophoresis to determine the sequence.

Sequencing of polynucleotides may be performed using either single-stranded or double stranded DNA. Use of polymerase for primer extension requires a single-stranded DNA template. In preferred embodiments, the method of the present invention uses double-stranded DNA in order to obtain confirmatory opposite strand confirmation of sequencing results. Double stranded DNA templates may be sequenced using either alkaline or heat denaturation to separate the two complementary DNA templates into single strands. During polymerization, each molecule of the DNA template is copied once as the complementary primer-extended strand. Use of thermostable DNA polymerases (e.g. Taq, Bst, Tth or Vent DNA polymerase) enables repeated cycling of double-stranded DNA templates in the sequencing reaction through alternate periods of heat denaturation, primer annealing, extension and dideoxy termination. This cycling process effectively amplifies small amounts of input DNA template to generate sufficient template for sequencing.

Sequencing may also be performed directly on PCR amplification reaction products. Although the cloning of amplified DNA is relatively straightforward, direct sequencing of PCR products facilitates and speeds the acquisition of sequence information. As long as the PCR reaction produces a discrete amplified product, it will be amenable to direct sequencing. In contrast to methods where the PCR product is cloned and a single clone is sequenced, the approach in which the sequence of PCR products is analysed directly is generally unaffected by the comparatively high error rate of Taq DNA polymerase. Errors are likely to be stochastically distributed throughout the molecule. Thus, the overwhelming majority of the amplified product will consist of the correct sequence. Direct sequencing of PCR products has the advantage over sequencing cloned PCR products in that (1) it is readily standardized because it is simple enzymatic process that does not depend on the use of living cells, and (2) only a single sequence needs to be determined for each sample.

The amplification methods used in the present invention may also be simultaneously used in conjunction with sequencing. Methods for simultaneous amplification and sequencing are widely known in the art, and include coupled amplification and sequence (CAS) (described by Ruano and Kidd, Proc. Nat'l. Acad. Sci. (USA) 88(7): 2815-2819 (1991), and in U.S. Pat. No. 5,427,911, which are incorporated herein by reference), and CLIP amplification and sequencing (described in U.S. Pat. No. 6,007,983, and in J. Clin. Microbiology 41(4); 1586-1593 (April 2003) which are incorporated herein by reference). CLIP sequencing subjects PCR amplification fragments previously generated to simultaneous PCR amplification and direct sequencing. In CAS sequencing, a sample is treated in a first reaction stage with two primers and amplified for a number of cycles to achieve 10,000 to 100,000-fold amplification. A ddNTP is then added during the exponential phase of the amplification reaction, and the reaction is processed for additional thermal cycles to produce chain-terminated sequencing fragments. The CAS process requires an intermediate addition of reagents (the ddNTP reagents), which introduces opportunity for error or contamination and increases the complexity of any apparatus which would be used for automation. The CAS methodology is therefore preferably combined with CLIP sequencing, which subjects PCR amplification fragments previously generated to simultaneous PCR amplification and direct sequencing. Simultaneous amplification and sequencing using the CLIP® method may be accomplished, for example, using the reagents described herein, under conditions similar to those described in commercially available kits, such as the TRUGENE® HCV genotyping kit (Bayer HealthCare LLC).

In particular aspects, the present invention relates to sequencing of HCV. The double stranded DNA template used in the method of the present invention may be derived from, for example, DNA or RNA, including messenger RNA, which may be single stranded or double stranded. In addition, the DNA template may be in the form of a DNA-RNA hybrid which contains one strand of DNA and one strand of RNA. A mixture of any of these nucleic acids may also be employed, or the nucleic acids produced from a previous amplification cation reaction herein using the same or different primers may be so utilized. The specific nucleic acid sequence to be amplified may be only a fraction of a larger molecule or can be present initially as a discrete molecule, so that the specific sequence constitutes the entire nucleic acid.

Genotyping HCV

The present invention includes a novel method and reagents for genotyping HCV in a sample suspected of containing or known to contain HCV.

The present invention addresses the above-mentioned problem, by providing primers that encompass a region of HCV.

The sequencing primers of the present invention consist of oligonucleotides specific to the NS5b region of HCV, which can be used to amplify and sequence a portion of HCV. In accordance with methods known to those in the art, a sample obtained from an individual suspected of being infected with HCV is used to recover viral RNA, either in the form of RNA or DNA. Viral HCV RNA obtained from the sample is reverse transcribed to cDNA. The cDNA template is then amplified, using Polymerase Chain Reaction or some other primer extension based method. The resulting amplified fragment is then initially sequenced with a set of primers the encompass the desired NS5b region of HCV using cycle sequencing methods or CLIP™ bi-directional sequencing.

One particular aspect of the present invention is a method for amplifying and genotyping a portion of the NS5b region of HCV in a sample suspected of containing HCV.

Sequencing of HCV

The present invention is generally directed to improved methods and reagents for genotyping a hepatitis C virus (HCV) species found in a test sample. In certain aspects of the invention, the invention relates to a method of sequencing a portion of the NS5B region of an HCV species in a sample and determining its genotype.

Generally, the invention relates to a method for determining the genotype of a hepatitis C virus (HCV) species present in a test sample by sequencing at least a portion of the NS5B region of HCV that, for each of a plurality of HCV species, is indicative of the type and/or subtype of that species.

The present invention also includes a method and primers for determining the sequence of the NS5b region of HCV, or a portion thereof. The sequencing primers of the present invention include both forward primers and reverse primers, which may be labeled with a detectable label. For most common sequencing instruments, a fluorescent label is desirable, although other labels types including colored, chromogenic, fluorogenic (including chemiluminescent) and radiolabels could also be employed. The primer combination may include other reagents appropriate for reverse transcription, amplification or sequencing, and may, of course, include HCV genetic material for analysis.

Although the sequencing primers of the present invention disclosed below are preferably selected from among primers having the same sequence as disclosed below, it is contemplated that the present invention includes degenerate sequences having the equivalent specificity and function, which may be designed and constructed in accordance with the skill in the art. Specifically, the sequencing primers include fragments of the above primers of 15 or more nucleotides. The sequencing primers may also include fragments of the above primers having 16, 17, 18, 19, or 20 or more nucleotides. The design and construction of such degenerate sequences is well know to those in the art.

Because sequencing primers, as opposed to amplification primers, may not be mixed together if they do not have the same location for the 3' base, only specific degenerate base positions are illustrated below, although it is to be understood that the 3' location may also be modified. For example, 5' length may be changed to include regions of greater sequence conservation or to modify melting temperature and stringency of binding. A nondegenerate primer set is preferred if the success rate is found to be sufficient with the primary primers. Reaction conditions may also significantly affect performance. The potential modifications of sequencing primers are illustrated in the following sections and examples.

In one embodiment, the method of the invention includes first determining the nucleotide sequence of at least a portion of the NS5b region of HCV indicative of the genotype of said HCV species. The portion of the NS5b region of HCV that is indicative of its genotype will be the same region that corresponds to the nucleotide sequence of a plurality of HCV species that is indicative of the genotype of each of the plurality of HCV species. Thus, one aspect of the invention is the identification of a region that is common among HCV species that is indicative of the type and/or subtype of the particular HCV species. Sequencing of this region of any HCV species thus enables determination of the type and subtype of that species, by correlating the nucleotide sequence of said portion of the NS5b region determined in the above step with the genotype of one of a plurality of HCV species of known sequence/genotype.

In another embodiment, the method comprises (a) determining the nucleotide sequence of at least a portion of the NS5b region of HCV indicative of the genotype of said HCV species, wherein the corresponding nucleotide sequence of each HCV species having genotypes 1, 2, 3, 4, 5, and 6 is indicative of the genotype of said species; and (b) correlating the nucleotide sequence of said portion of the NS5b region determined in (a) with one of HCV genotypes 1, 2, 3, 4, 5 and 6.

In yet another embodiment, the method comprises (a) determining the nucleotide sequence of at least a portion of the NS5b region of HCV indicative of the genotype and subtype of said HCV species, wherein the corresponding nucleotide sequence of each HCV species having genotypes 1, 2, 3, 4, 5, and 6, and each of the subtypes set forth in Table 1, is indicative of the genotype and subtype of said species; and (b) correlating the nucleotide sequence of said portion of the NS5b region determined in (a) with one of HCV genotypes 1, 2, 3, 4, 5 and 6 and one of the subtypes set forth in Table 1.

In one particular embodiment of the above methods, the portion of the NS5b region of HCV consists essentially of the region from about nucleotide position 8344 to about 8547 shown in FIG. 2.

In another particular embodiment of the above methods, the portion of the NS5b region of HCV consists essentially of the region from nucleotide position 8344 to 8547 shown in FIG. 2.

In another embodiment, the method of present invention comprises (a) providing a mixture of degenerate oligonucleotide sequencing primers capable of generating nucleotide sequence of at least a portion of the NS5b region of a plurality of HCV species, and wherein the corresponding nucleotide sequence of each of said plurality of HCV species is indicative of the genotype of said species; (b) determining the nucleotide sequence of said portion of the NS5b region indicative of the genotype of said species; and (c) correlating the nucleotide sequence of said portion of the NS5b region of said HCV species determined in (b) with a genotype of one of said plurality of HCV species.

In yet another embodiment, the method comprises (a) providing a mixture of degenerate oligonucleotide sequencing primers capable of generating nucleotide sequence of at least a portion of the NS5b region of a plurality of HCV species, wherein the corresponding nucleotide sequence of each of said plurality of HCV species is indicative of one of HCV genotypes 1, 2, 3, 4, 5 and 6; (b) determining the nucleotide sequence of said portion of the NS5b region indicative of the genotype of said species; and (c) correlating the nucleotide sequence of said portion of the NS5b region of said HCV species determined in (b) with one of HCV genotypes 1, 2, 3, 4, 5 and 6.

In still another embodiment, the method comprises (a) providing a mixture of degenerate oligonucleotide sequencing primers capable of generating nucleotide sequence of at least a portion of the NS5b region of a plurality of HCV species, wherein the corresponding nucleotide sequence of each of said plurality of HCV species is indicative of one of HCV genotypes 1, 2, 3, 4, 5 and 6 and one of the subtypes set forth in Table 1; (b) determining the nucleotide sequence of said portion of the NS5b region indicative of the genotype of said species; and (c) correlating the nucleotide sequence of said portion of the NS5b region of said HCV species determined in (b) with an HCV genotype and subtype (for example, one of HCV genotypes 1, 2, 3, 4, 5 and 6 and one of the subtypes set forth in Table 1).

In one particular embodiment, the mixture of degenerate oligonucleotide sequencing primers comprises degenerate nucleotide sequences complementary to the NS5b region of a plurality of HCV species from about nucleotide 8256 to about 8278 (for example, CLIP sequencing primer M-NS5b-Cy5.5) shown in FIG. 2, or its complement, and degenerate nucleotide sequences complementary to the NS5b region of a plurality of HCV species from about nucleotide 8611 to about 8633 (for example, CLIP sequencing primer M-NS5b-Cy5) shown in FIG. 2, or its complement.

In another particular embodiment, the mixture of degenerate oligonucleotide sequencing primers comprises degenerate nucleotide sequences complementary to the NS5b region of a plurality of HCV species from nucleotide 8256 to 8278 (for example, CLIP sequencing primer M-NS5b-Cy5.5) shown in FIG. 2, or its complement, and degenerate nucleotide sequences complementary to the NS5b region of a plurality of HCV species from nucleotide 8611 to 8633 (for example, CLIP sequencing primer M-NS5b-Cy5) shown in FIG. 2, or its complement.

In yet another particular embodiment, the mixture of degenerate oligonucleotide sequencing primers comprise degenerate oligonucleotide sequences defined by one or more of the following formulas, or complements thereof:

```
SEQ ID NO: 1: 5'-TAT GAY ACC CGC TGY TTY GAY
TC-3';
and

SEQ ID NO: 2: 5'-VGT CAT RGC ITC YGT RAA GGC
TC-3'.
```

Other variations of the above sequences may be utilized to permit detection of other HCV variants.

Example 1

HCV NS5b Genotyping by Sequencing

This following example describes a laboratory protocol to produce bi-directional sequence of a 204 base pair fragment in the NS5b region of Hepatitis C virus for the purpose of determining genotype and subtype.

Generally, viral HCV RNA is extracted from the plasma sample using a Qiagen QIAamp Viral RNA Mini Kit as described by the manufacturer. Briefly, the extracted RNA specimens are reverse transcribed using random hexamers.

Following cDNA synthesis, 10 µL of the cDNA template is amplified using specific primers to generate a 398 base pair amplicon.

Following PCR amplification, a dye-primer CLIP sequencing reaction is performed. The CLIP reaction sequences both strands of the DNA simultaneously by using forward (sense) and reverse (antisense) primers each labeled with different fluorescent dyes (Cy 5.5, Cy 5; chain-extension reagents, and one of four chain-terminating dideoxynucleotide triphosphates (ddNTPs): dideoxyadenosine (ddATP), dideoxycytidine (ddCTP), dideoxyguanosine (ddGTP), or dideoxythymidine (ddTTP) triphosphates. The reaction is initiated with the addition of the sample and a thermostable DNA polymerase with a high affinity for ddNTPs. As the reaction mixture is thermally cycled, primers hybridize to template DNA and are extended, then usually terminated somewhere along the target DNA sequence. Four CLIP reactions yield both the forward and reverse sequence of the target between the two CLIP primers. The reaction proceeds through 40 cycles generating high levels of chain terminated reaction products from each primer. Upon completion of the cycling program, Stop Loading Dye solution is added to each reaction tube and the reactions are heated to separate the double-stranded DNA fragments. A fraction of each reaction is then loaded onto the top of a MicroCel™ 500 cassette containing an ultra thin vertical polymerized polyacrylamide gel that has a formed matrix of specific pore size. The polyacrylamide gel contains a high concentration of urea to maintain the DNA fragments in a single-stranded denatured state. A buffered solution maintains contact with both the top and bottom of the ultra thin gel. A high voltage electric field is applied, forcing the negatively charged fragments of DNA to migrate through the gel towards the anode. The speed of migration of the DNA fragments is related to the size of pores formed by the polyacrylamide matrix and DNA fragment size, with the smaller fragments migrating faster. Near the bottom of the polyacrylamide gel, a laser beam excites the fluorescent dye linked to the DNA fragments moving past the laser, and detectors measure the amount of light and wavelength produced by the fluorescent dye. This light measurement is then collected by the sequencer and transmitted to a workstation that stores the data. Each sequencing reaction requires four lanes, one for each of the four chain terminating dideoxynucleotides. (ddATP, ddCTP, ddGTP, ddTTP). The forward and reverse CLIP sequences are combined and compared to the sequence of a "best matched" reference sequence (W). Operators review the alignment at flagged positions and edit the bases as necessary. The software prepares an HCV NS5b report for each sample.

Reverse Transcription (cDNA synthesis)

cDNA is synthesized from genomic RNA derived from the sample in accordance with the following protocol.

RT reagents described below (except SuperScript and RNase inhibitor) are vortexed and microcentrifuged to recover volume. The HCV NS5b RT Master Mix is prepared, using volumes calculated according to the following formula:

| HCV NS5b RT Master Mix | | |
| --- | --- | --- |
| RT Reagent | Final Conc. | Volume/sample |
| Nuclease free water | | 3.90 µL |
| 10X PCR Buffer II | 1X | 2.50 µL |
| MgCl2 Solution (25 mM) | 5 mM | 5.00 µL |
| dNTP's (100 mM) | 8 mM | 2.00 µL |
| Random Hexamers | 60 pg/µL | 1.00 µL |
| RNase Inhibitor (20 U/µL) | 0.4 U/µL | 0.50 µL |
| SuperScript III Reverse Transcriptase (200 U/µL) | 0.8 U/µL | 0.10 µL |
| TOTAL RT reagent | | 15.00 µL |

RT reagents (15 µL) are aliquoted into each labeled PCR tube. Tubes are transferred to post amplification area dead air hood. Sample and control RNA extracts are removed from freezer to thaw at room temperature. Thawed RNA extract (10 µL) is added to the appropriate tube containing the RT reagent. The reagent and RNA are mixed by gently tapping tray.

The tubes are placed in a thermocycler programmed to perform the following steps:

| HCV NS5b RT Program | | | |
| --- | --- | --- | --- |
| # Cycles | Min | Temp ° C. | Process |
| 1 | 10 | 25 | Random Hexamer annealing |
| 1 | 30 | 50 | Reverse Transcription |
| 1 | 15 | 75 | SuperScript de-activation |
| 1 | Forever | 4 | Hold |

RT samples are removed from the thermocycler and stored at 4° C.

PCR Amplification

Amplification by polymerase chain reaction (PCR) is performed as follows. PCR tubes are prepared and labeled for samples. PCR reagents described below (except AmpliTaq Gold enzyme) are vortexed and microcentrifuged to recover volume. Mixtures of degenerate primers, which are designed to amplify multiple clinically relevant HCV species, are prepared, having the following nucleotide sequences:

```
                                            (SEQ ID NO: 7)
Forward PCR Primer (FF-1): 5'-TGG GGT TCK CGT ATG
AYA CCC GCT G-3'

(SEQ ID NO: 8)
Forward PCR Primer (FF-2): 5'-TGG GGT TCK CIT ATG
AYA CYM GIT G-3'

(SEQ ID NO: 9)
Reverse PCR Primer (RR1): 5'-GAR TAY CTV GTC ATR
GCI TCY GTR AA-3'
```

A PCR Master Mix is prepared using the worksheet for reagent volumes. Volumes are calculated according to the following formula:

| HCV NS5b PCR Mastermix | | |
| --- | --- | --- |
| PCR reagent | Final Concentration | Volume per sample |
| Nuclease free water | | 23.25 µL |
| 10X PCR Buffer II | 0.8 X | 4.00 µL |
| 25 mM MgCL2 Solution | 1 mM | 2.00 µL |
| M-NS5B-FF1 (10 µM) | 0.3 µM | 1.50 µL |
| M-NS5B-FF2 (10 µM) | 0.6 uM | 3.00 uL |

HCV NS5b PCR Mastermix

| PCR reagent | Final Concentration | Volume per sample |
|---|---|---|
| M-NS5B-RR1 (10 µM) | 1.2 µM | 6.00 µL |
| AmpliTaq Gold (5 U/µL) | 0.025 U/µL | 0.25 µL |
| TOTAL PCR reagent | | 40.00 µL |

The PCR Master Mix (40 µL) is aliquoted into each labeled PCR tube. RT cDNA (10 µL) is added to appropriately labeled tubes containing PCR reagent, and tubes are placed in a thermocycler programmed to perform the following steps:

HCV NS5b PCR Program

| # cycles | Time | Temp ° C. | Process |
|---|---|---|---|
| 1 | 10 min | 95 | AmpliTaq activation |
| 45 | 30 sec | 94 | Denaturation |
|  | 30 sec | 48 | Annealing |
|  | 1 min | 68 | Extension |
| 1 | 10 min | 68 | Final Extension |
| 1 | Forever | 4 | Hold |

PCR samples are removed from the thermocycler, and may be stored at 4° C. for up to two weeks or subjected to CLIP sequencing, as described below.

CLIP Sequencing

Mixtures of degenerate sequencing primers, which are designed to sequence multiple clinically relevant HCV species, are prepared, having the following nucleotide sequences:

```
                                        (SEQ ID NO: 10)
Forward CLIP Primer: 5'Cy5.5-5'TAT GAY ACC CGC TGY
TTY GAY TC-3'

(SEQ ID NO: 11)
Reverse CLIP Primer: Cy5-5'-VGT CAT RGC ITC YGT
RAA GGC TC-3'
```

The necessary number of PCR strip tubes and caps is assembled in a tray and place in a cold block. A 0.5 mL tube is labeled for each sample and control and place in cold block. CLIP reagents (except Thermo Sequenase enzyme) are removed from the freezer, and thawed at room temperature. Each component (except Thermo Sequenase enzyme) is vortexed and quick spin to recover volume. Using a 10 µl, adjustable pipet, 3 µL of the appropriate CLIP terminator mixes is transferred directly to the bottom of the respective column of wells in each of the PCR tubes.

A 1:10 dilution of Thermo Sequenase enzyme in Thermo Sequenase Dilution Buffer is made. The CLIP Master Mix is prepared using reagent volumes calculated according to the following formula:

HCV NS5b CLIP Master Mix

| CLIP reagent | Final Concentration | Volume per sample |
|---|---|---|
| Nuclease free water | | 6.50 µL |
| 7-Deaza-dGTP Cy5/Cy5.5 Dye Primer Cycle Sequencing Kit (100 tests) | 1X | 2.50 µL |
| Thermo Sequenase Dilution Buffer (520 µL) | | |
| Thermo Sequenase Enzyme (57 µL) | | |
| Sequencing Buffer (320 µL) | | |
| A Termination Mix (375 µL) | | |
| C Termination Mix (375 µL) | | |
| G Termination Mix (375 µL) | | |
| T Termination Mix (375 µL) | | |
| Stop Loading Dye (2750 µL) | | |
| M-NS5B Forward CLIP Primer | 0.4 µM | 2.50 µL |
| M-NS5B Reverse CLIP Primer | 0.1 µM | 2.50 µL |
| DMSO | 8% | 2.00 µL |
| Themo Sequenase enzyme 1:10 dilution | 0.512 U/µL | 4.00 µL |
| TOTAL CLIP reagent | | 20.00 µL |

20 µL CLIP Master Mix are aliquoted into each labeled tube and transferred to tubes containing CLIP reagents. The PCR amplicon (2 µL) is added to appropriate tubes containing the CLIP Master Mix, vortex briefly and microcentrifuged to collect volume at bottom of tube. The CLIP mix (5 µL) is added to each of the 4 terminator tubes in the cold block The CLIP amplification/sequencing reaction is performed on a thermocycler in accordance with the following protocol:

HCV NS5b CLIP

| # cycles | Time | Temp ° C. | Process |
|---|---|---|---|
| 1 | 2 min | 94 | Initial denaturation |
| 25 | 20 sec | 94 | Denaturation |
|  | 45 sec | 45 | Annealing |
|  | 1 min | 68 | Extension |
| 15 | 25 sec | 94 | Denaturation |
|  | 2 min | 70 | Annealing and extension |
| 1 | 2 min | 72 | Final extension |
| 1 | forever | 4 | Hold |

Tubes are removed from the thermocycler and add Stop Loading Dye (6 µL) is added to each tube, and vortexed to mix. The tubes are returned to the thermocycler and subjected to denature conditions, as follows:

HCV NS5b Denature

| # cycles | Time | Temp ° C. | Process |
|---|---|---|---|
| 1 | 2 min | 80 | Denaturation |
| 1 | Forever | 4 | Hold |

Tubes are remove from the thermocycler and stored or subjected to gel electrophoresis, as described below.

Gel Electrophoresis is performed using a Long-Read Tower Sequencer, as described by the manufacturer, using the following sequencer control settings:

| Gel Temperature (° C.) | 60° C. |
|---|---|
| Gel Voltage (V) | 1800 V |
| Laser Power (%) | 50% |
| Run Clock (Sampling Interval) | 0.5 sec |
| Run Clock (Run Duration) | 50 min |

Assays are assigned with sample and control information.

Example 2

Evaluation of Performance Characteristics of HCV NS5b Genotyping By Sequencing The performance characteristics of HCV NS5b genotyping assay were evaluated, based on genotyping assays substantially as described above in Example 1, using the following reagents.

| HCV NS5b Specific Reagents | |
|---|---|
| Description | Lot # |
| M-NS5b-FF1 | Oct. 27, 2004 |
| M-NS5b-FF2 | Dec. 27, 2004 |
| M-NS5b-RR1 | Oct. 27, 2004 |
| M-NS5bSes-Cy5.5 | Oct. 27, 2004 |
| M-NS5bSeq-Cy5 | Oct. 27, 2004 |

Table 1

| General Purpose Reagent's | |
|---|---|
| Description | Lot # |
| PCR Buffer II | E10896 |
| 25 mM MgCl2 | E10900 |
| dNTP 100 mM | 36227107050 |
| Random Hexamers | F06662 |
| RNase Inhibitor | F07872 |
| SuperScript III RT | 1232439 |
| AmpliTaq Gold | E11258 |
| DMSO | R19030 |
| SureFill 6% Sequencing Gel | 0294B94 |
| MicroCel 500 | 2624 |
| Cy5.5/5 Cycle Sequencing Kit containing the following: | 01609 |
| Sequencing Buffer | |
| ThermoSequenase Enzyme | |
| ThermoSequenase Dilution Buffer | |

The following samples were used:

| | | | Samples | | |
|---|---|---|---|---|---|
| HCV Genotype (LiPA TMA LiPA) | HCV Genotype (TRUGENE 5'NC) | HCV Genotype (NS5B) | Specimen ID | Viral Load (c/mL) | Vendor |
| | | 1 | Acrometrix 1 | | Acrometrix |
| | | 2b | Acrometrix 2 | | Acrometrix |
| | | 3a | Acrometrix 3 | | Acrometrix |
| | | 4a | Acrometrix 4 | | Acrometrix |
| | | 5a | Acrometrix 5 | | Acrometrix |
| | | 6a | Acrometrix 6 | | Acrometrix |
| 1a 1a | 1 | | MP 1 | | Millenium |
| 1a 1a | 1a | | MP 2 | | Millenium |
| 1a 1a | 1a | | MP 3 | | Millenium |
| 1a 1a | 1a | | MP 4 | | Millenium |
| 1a 1a | 1a | | MP 5 | | Millenium |
| 1b 1b | 1b | | MP 6 | | Millenium |
| 1b 1b | 1b | | MP 7 | | Millenium |
| 1b 1b | 1b | | MP 8 | | Millenium |
| 1b 1b | 1 | | MP 9 | | Millenium |
| 1b 1b | 1b | | MP 10 | | Millenium |
| 2 2b 2 | 2b | | MP 11 | | Millenium |
| 2 2b 2 | 2b | | MP 12 | | Millenium |
| 2 2b 2 | 2b | | MP 13 | | Millenium |
| 2 2b 2 | 2b | | MP 14 | | Millenium |
| 2 2b 2 | 2b | | MP 15 | | Millenium |
| 3a 3a | 3a | | MP 16 | | Millenium |
| 3a 3a | 3a | | MP 17 | | Millenium |
| 3a 3a | 3d | | MP 18 | | Millenium |
| 1a 1a | 1a | | MP 19 | | Millenium |
| 4 4 | 4a | | MP 20 | | Millenium |
| 4c/4d 4c/4d | 4a | | MP 21 | | Millenium |
| 3a 3a | 3a | | MP 22 | | Millenium |
| 4h 4 | 4a | | MP 23 | | Millenium |
| 5a 5a | 5a | | MP 24 | | Millenium |
| 5a 5a | 5a | | MP 25 | | Millenium |
| 1A | | | GP1A-C2 | 10,000 | Bayer Clinical Affairs |
| 1B | | | GP1B-A2 | 10,000 | Bayer Clinical Affairs |
| | | 2A | 9810067 | 2,292,000 | Bayer Clinical Affairs |
| | | 2A | GP2A-A2 | 10,000 | Bayer Clinical Affairs |
| | | 2A | GP2A-B2 | 10,000 | Bayer Clinical Affairs |
| | | 2A | GP2A-C2 | 10,000 | Bayer Clinical Affairs |
| | | 2B | GP2B-A2 | 10,000 | Bayer Clinical Affairs |

-continued

| HCV Genotype (LiPA TMA LiPA) | HCV Genotype (TRUGENE 5'NC) | HCV Genotype (NS5B) | Specimen ID | Viral Load (c/mL) | Vendor |
|---|---|---|---|---|---|
| 3A | | 3A | 3-3A | 30,043,850 | Bayer Clinical Affairs |
| | 4A | | GP4A-A2 | 10,000 | Bayer Clinical Affairs |
| | 4A | | GP4A-B2 | 10,000 | Bayer Clinical Affairs |
| | | 4A | GP4A-C2 | 10,000 | Bayer Clinical Affairs |
| | 5A (Sequetech) | | 1-5A | 9,745,338 | Bayer Clinical Affairs |
| 6A | | | GP6A-A2 | 10,000 | Bayer Clinical Affairs |
| 6A | | | GP6A-A3 | 5,000 | Bayer Clinical Affairs |
| 6A | | | 2-6A (24485) | 11,168,451 | Bayer Clinical Affairs |
| | 6A (Sequetech) | | GP6A-C2 | 10,000 | Bayer Clinical Affairs |
| | 6A (Sequetech) | | GP6A-C3 | 5,000 | Bayer Clinical Affairs |
| | 4A | | 14682 | 1,326,000 | Teragenix |
| 5A | | | 15038 | 2,522,000 | Teragenix |
| 6A | | | 20759 | 8,112,000 | Teragenix |
| | | 7C | HCVGTP-004c #1 | 17,628,000 | Teragenix |
| | | 9B | HCVGTP-004c #2 | 10,660,000 | Teragenix |
| | | 8C | HCVGTP-004c #3 | 45,240,000 | Teragenix |
| | | 6B | HCVGTP-004c #4 | 1,237,000 | Teragenix |
| | | 7C | HCVGTP-004c #5 | 31,824,000 | Teragenix |
| | | 10A | HCVGTP-004a #1 | 7,852,000 | Teragenix |
| | | 8C | HCVGTP-004a #2 | 25,584,000 | Teragenix |
| | | 10A | HCVGTP-004a #3 | 19,032 | Teragenix |
| | | 9B | HCVGTP-004a #4 | 14,248,000 | Teragenix |
| neg | neg | | M60825 negative diluent | | Bayer Clinical Affairs |
| neg | neg | | HCV negative control (Jan. 29, 2004) | | Bayer Clinical Affairs |
| | | neg | M60789 negative diluent | | Bayer Clinical Affairs |
| | 1b | | positive control | | Cntrol |

Analytical Accuracy Analysis

In order to determine the analytical accuracy of the methods and reagents of the invention, an analysis was performed using a 25 member panel comprising genotypes 1-5, a 6 member panel comprising genotypes 1-6, a 12 member panel comprising genotypes 4-10, and 15 additional clinical samples comprising genotypes 1-6 were analyzed and results compared to previous genotype.

Samples were genotyped using the methodology described in Example 1, above, and were compared with the genotype of the same samples, as previously characterized by either LiPA or TruGene 5'NC genotyping or another NS5b method as detailed in the samples section, to determine analytical accuracy. The results of this analysis are summarized in the following table:

Analytical Accuracy Data

| Sample ID | Expected Genotype (new nomenclature) | BRTL NS5B Genotype |
|---|---|---|
| MP 1 | 1a | 1a |
| MP 2 | 1a | 1a |
| MP 3 | 1a | 1a |
| MP 4 | 1a | 1a |
| MP 5 | 1a | 1a |
| MP 6 | 1b | 1b |
| MP 7 | 1b | 1b |
| MP 8 | 1b | 1b |
| MP 9 | 1b | 1a |
| MP 10 | 1b | 1b |
| MP 11 | 2b | 2b |
| MP 12 | 2b | 2b |
| MP 13 | 2b | 2b |
| MP 14 | 2b | 2b |
| MP 15 | 2b | 2b |
| MP 16 | 3a | 3a |
| MP 17 | 3a | UG rpt 3a |
| MP 18 | 3a | 3a |
| MP 19 | 1a | 1a |
| MP 20 | 4a | 4a |
| MP 21 | 4a | 4a |
| MP 22 | 3a | UG (hets) rpt 3a |
| MP 23 | 4a | 4a |
| MP 24 | 5a | 5a |
| MP 25 | 5a | 5a |
| Acrometrix 1 | 1b | 1a |
| Acrometrix 2 | 2b | 2b |
| Acrometrix 3 | 3a | 3a |
| Acrometrix 4 | 4 | 4a |

Analytical Accuracy Data

| Sample ID | Expected Genotype (new nomenclature) | BRTL NS5B Genotype |
|---|---|---|
| Acrometrix 5 | 5a | 5a |
| Acrometrix 6 | 6a | UG |
| HCVGTP-004c #1 | 7c (6f) | UG |
| HCVGTP-004c #2 | 9b (6i) | 6i |
| HCVGTP-004c #3 | 8c (6n) | 6n |
| HCVGTP-004c #4 | 6b | 6b |
| HCVGTP-004c #5 | 7c (6f) | UG |
| HCVGTP-004a #1 | 10a (3k) | 3k |
| HCVGTP-004a #2 | 8c (6n) | 6n |
| HCVGTP-004a #3 | 10a (3k) | 3k |
| HCVGTP-004a #4 | 9b (6i) | 6i |
| 14682 | 4a | 4a |
| 15038 | 5a | 5a |
| 20759 | 6a | UG |
| GP1A-C2 (10,000 c/mL) | 1a | 1a |
| GP1B-A2 (10,000 c/mL) | 1b | 1a rpt 1a |
| 9810067 (2,292,000 c/mL) | 2a | 2a |
| GP2A-A2 (10,000 c/mL) | 2a | 2a rpt 2a |
| GP2A-B2 (10,000 c/mL) | 2a | 2a rpt 2a |
| GP2A-C2 (10,000 c/mL) | 2a | 2a |
| GP2B-A2 (10,000 c/mL) | 2b | 2b rpt 2b |
| 3-3A (30,043,850 c/mL) | 3a | 3a |
| GP4A-A2 (10,000 c/mL) | 4a | 4a |
| GP4A-B2 (10,000 c/mL) | 4a | 4a |
| 2-6A (24485) (11,168,451 c/mL) | 6a | UG |
| GP4A-C2 (10,000 c/mL) | 4a | 4a |
| 1-5A (9,745,338 c/mL) | 5a | 5a |
| GP6A-A2 (10,000 c/mL) | 6a | UG |
| GP6A-C2 (10,000 c/mL) | 6a | UG |

A total of 58 accuracy samples analyzed yielded 51 NS5b genotype results. 51 of 51 or 100% of samples genotypable with NS5b yielded a genotype concordant with previously determined genotype at type level. 48 of 51 samples were concordant at both type and subtype level, and 3 of 51 samples were concordant at type level only (all 3 were 1b by LiPA and 1a by NS5b). 7 samples (5 genotype 6a and 2 genotype 7c) failed amplification and were unable to be genotyped by NS5b.

The above data demonstrates that the accuracy of the genotyping assay of the invention is superior to other commercially available assays. The assay showed 100% concordance with previous genotype result at the type level for 51 samples that were genotypable with NS5b. Seven samples that were ungenotypable with NS5b were excluded from this phase of the evaluation. All 7 ungenotypable samples were repeated in Phase 2 of this evaluation.

An alternate set of RT-PCR primers is in development to amplify genotype 6a and 7c, was subsequently designed and analyzed, as described below in connection with the Phase 2 analysis.

Reproducibility Analysis

In order to determine the reproducibility of the HCV NS5b genotyping assay and reagents of the invention, a total of 22 samples comprising genotypes 1-10 were analyzed by two operators on two separate runs and results compared for concordance at the type and subtype level. The results of positive controls on each of the eight runs was also compared.

Operator to Operator Reproducibility Data

| Sample ID | Operator 1 NS5b Genotype | Operator 2 NS5b Genotype |
|---|---|---|
| HCVGTP-004c #1 | UG | UG |
| HCVGTP-004c #2 | 6i | 6i |
| HCVGTP-004c #3 | 6n | 6n |
| HCVGTP-004c #4 | 6b | 6b |
| HCVGTP-004c #5 | UG | UG |
| HCVGTP-004a #1 | 3k | 3k |
| HCVGTP-004a #2 | 6n | 6n |
| HCVGTP-004a #3 | 3k | 3k |
| HCVGTP-004a #4 | 6i | 6i |
| 14682 | 4a | 4a |
| 15038 | 5a | 5a |
| 20759 | UG | UG |
| Acrometrix 1 | 1a | 1a |
| Acrometrix 2 | 2b | 2b |
| Acrometrix 3 | 3a | 3a |
| Acrometrix 4 | 4a | 4a |
| Acrometrix 5 | 5a | 5a |
| Acrometrix 6 | UG | UG |
| GP4A-C2 | 4a | 4a |
| 1-5A | 5a | 5a |
| GP6A-A2 | UG | UG |
| GP6A-C2 | UG | UG |

Run to Run Reproducibility Data

| Sample ID | Expected genotype | BRTL NS5b Genotype |
|---|---|---|
| Positive control run 1 | 1b | 1b |
| Positive control run 2 | 1b | 1b |
| Positive control run 3 | 1b | 1b |
| Positive control run 4 | 1b | 1b |
| Positive control run 5 | 1b | 1b |
| Positive control run 6 | 1b | 1b |
| Positive control run 7 | 1b | 1b |
| Positive control run 8 | 1b | 1b |

22 samples were analyzed separately by two operators, yielding 16 NS5b genotypes. The above data demonstrates that the NS5b genotyping assay resulted in 16/16 or 100% concordance of NS5b genotypes at both type and subtype level between two operators, as well as between two runs.

6 samples (4 genotype 6a and 2 genotype 7c) were unable to be amplified or genotyped by both operators. Run to Run reproducibility: 100% concordance among 8 replicates of positive control from 8 runs.

Sensitivity Analysis

In order to determine the level of sensitivity of the genotyping assay, a dilution panel of genotypes 1-10 was also prepared as detailed below HCV NS5b Sensitivity Dilution Panel

| Genotype | nominal c/mL | # replicates tested | # replicates genotypable |
|---|---|---|---|
| 1a | 5,000 | 3 | 3/3 |
| 1a | 1,000 | 6 | 3/6 |
| 1a | 500 | 6 | 0/6 |
| 2b | 5,000 | 3 | 3/3** |
| 2b | 1,000 | 6 | 6/6** |
| 2b | 500 | 6 | 4/6 |
| 3 | 1,000 | 3 | 3/3 |
| 4 | 1,000 | 3 | 1/3 |
| 5 | 1,000 | 3 | 3/3 |

HCV NS5b Sensitivity Dilution Panel

| Genotype | nominal c/mL | # replicates tested | # replicates genotypable |
|---|---|---|---|
| 6 | 1,000 | 3 | 0/3 |
| 6b (004c #4) | 2,423* | 3 | 0/3 |
| 7c (004c #1) | 258* | 3 | 0/3 |
| 7c (004c #5) | 101* | 3 | 0/3 |
| 8c (004c #3) | 182* | 3 | 0/3 |
| 8c (004a #2) | 665* | 3 | 0/3 |
| 9b (004c #2) | 283* | 3 | 0/3 |
| 9b (004a #4) | 1,372* | 3 | 0/3 |
| 10a (004a #1) | 1,743* | 3 | 3/3 |
| 10a (004a #3) | 1,000 | 3 | 0/3 |
| 4a (14682) | 571* | 1 | 0/1 |
| 5a (15038) | 368* | 1 | 0/1 |
| 6a (20759) | 343* | 1 | 0/1 |

*Sensitivity panel dilutions made based on Certificate of Analysis values supplied by vendor. Subsequent viral loads determined by bDNA were used to recalculate the nominal value for these sensitivity panel members.
**This sample is confirmed as a 2b by LiPA and HCV 5'NC TruGene genotyping and genotypes as a 1b with NS5b genotyping. It will be sent to a reference lab for additional testing to resolve genotype discrepancy.

The above data indicate that the HCV NS5b genotyping assay meets criteria for acceptable sensitivity for genotypes 1-5, as HCV genotype 1-5 samples were accurately and reproducibly genotyped at 1,000 c/mL (192 IU/mL).

The HCV NS5b genotyping assay did not, however, consistently genotype samples for HCV genotype 6. HCV genotype 6 samples were consistently ungenotypable at 1,000 c/mL (192 IU/mL). Accordingly, due to issues in preparing the sensitivity dilutions for genotype 6-10, sensitivity at 1,000 c/mL can not be determined from this data. The NS5b genotyping assay is therefore accurate at 1,000 c/mL for genotypes 1-5 with variable consistency.

Example 3

Evaluation of Performance Characteristics of HCV NS5b Genotyping By Sequencing

Analytical Accuracy Analysis

A subset of the phase 1 validation accuracy samples consisting of a 6 member panel comprising genotypes 1-6, a 12 member panel comprising genotypes 4-10, and 4 additional clinical samples comprising genotypes 4, 5 and 6 will be analyzed and results compared to previous genotype. Samples were previously characterized by either LiPA or TruGene 5'NC genotyping or another NS5b method as detailed in the samples section.

Analytical Accuracy Data

| Sample ID | Expected Genotype | BRTL NS5b Genotype |
|---|---|---|
| HCVGTP-004c #1 | 7C (6f) | 6f |
| HCVGTP-004c #2 | 9B (6i) | 6i |
| HCVGTP-004c #3 | 8C (6n) | 6n |
| HCVGTP-004c #4 | 6B | 6b |
| HCVGTP-004c #5 | 7C (6f) | 6f |
| HCVGTP-004a #1 | 10A (3k) | 3k |
| HCVGTP-004a #2 | 8C (6n) | 6n |
| HCVGTP-004a #3 | 10A (3k) | 3k |
| HCVGTP-004a #4 | 9B (6i) | 6i |
| 14682 | 4A | 4a |
| 15038 | 5A | 5a |
| 20759 | 6A | 6a |
| Acrometrix 1 | 1B | 1a |
| Acrometrix 2 | 2B | 2b |
| Acrometrix 3 | 3A | 3a |
| Acrometrix 4 | 4 | 4a |
| Acrometrix 5 | 5A | 5a |
| Acrometrix 6 | 6A | 6a |
| GP4A-C2 | 4A | UG (no amp) rpt 4a |
| 1-5A | 5A | 5a |
| GP6A-A2 | 6A | 6a |
| GP6A-C2 | 6A | 6a |

The above data indicates that the accuracy of the HCV NS5b genotyping assay is 100% concordant at the type level for all samples, including two 7c samples and four 6a samples that had previously failed.

Reproducibility Analysis

The results of positive controls on each of the four runs was compared, as follows:

Reproducibility Data

| Sample ID | Expected Genotype | BRTL NS5bGenotype |
|---|---|---|
| Positive control run 1 | 1b | 1b |
| Positive control run 2 | 1b | 1b |
| Positive control run 3 | 1b | 1b |
| Positive control run 4 | 1b | 1b |

The above data shows 100% concordance among 4 replicates of positive control from 4 runs Sensitivity Analysis A dilution panel of genotype 1-6 was prepared as detailed below:

Sensitivity Data

| Genotype ID | Nominal c/mL | # replicates tested | # replicates genotypable |
|---|---|---|---|
| 1a 5,000 | 5,000 | 3 | 3/3 |
| 1a 1,000 | 1,000 | 3 | 1/3 |
| 2b 5,000 | 5,000 | 3 | 3/3* |
| 2b 1,000 | 1,000 | 3 | 2/3* |
| 3 1,000 | 1,000 | 3 | 3/3 |
| 4 1,000 | 1,000 | 3 | 3/3 |
| 5 1,000 | 1,000 | 3 | 3/3 |
| 6 1,000 | 1,000 | 3 | 0/3 |
| 7c 004c #1 | 5,000 | 3 | 3/3 |
| 9b 004c #2 | 5,000 | 3 | 3/3 |
| 8c 004c #3 | 5,000 | 3 | 1/3 |
| 6b 004c #4 | 5,000 | 3 | 3/3 |
| 7c 004c #5 | 5,000 | 3 | 3/3 |
| 10a 004a #1 | 5,000 | 3 | 3/3 |
| 8c 004a #2 | 5,000 | 3 | 3/3 |
| 10a 004a #3 | 1,000 | 3 | 1/3 |
| 9b 004a #4 | 5,000 | 3 | 1/3 |
| 6a GP6a A3 | 5,000 | 3 | 1/3 |
| 6a GP6A C3 | 5,000 | 3 | 1/3 |
| 6a 20759 | 5,000 | 3 | 3/3 |

*This sample is confirmed as a 2b by LiPA and HCV 5'NC TruGene genotyping and genotypes as 1b with NS5b. It will be sent to a reference lab for additional testing to resolve genotype discrepancy.

This assay resulted in accurate and reproducible genotypes at 1,000 c/mL (192 IU/mL) for genotypes 1-5, as well as accurate and reproducible genotypes at 5,000 c/mL (962 IU/mL) for genotype 6.

What is claimed is:

1. A method for determining a genotype and subtype of a hepatitis C virus (HCV) species present in a test sample, comprising:
    (a) amplifying a portion of the NS5b region of a HCV species present in a test sample with a mixture of degenerate oligonucleotide PCR primers comprising degenerate oligonucleotide sequences defined by the following formulas:

SEQ ID NO: 6: 5'-TGG SBT TYK CNT AYG AYA CYM GNT G-3';
    and

SEQ ID NO: 9: 5'-GAR TAY CTV GTC ATR GCI TCY GTR AA-3';

(b) generating a nucleotide sequence of at least a portion of the amplified portion of the NS5b region with a mixture of degenerate oligonucleotide sequencing primers comprising degenerate oligonucleotide sequences defined by the following formulas:

SEQ ID NO: 1: 5'-TAT GAY ACC CGC TGY TTY GAY TC-3';
    and

SEQ ID NO: 2: 5'-VGT CAT RGC ITC YGT RAA GGC TC-3';
    and
    (c) correlating the nucleotide sequence determined in (b) with a subtype of one of HCV genotypes 1, 2, 3, 4, 5 and 6, thereby determining the genotype and subtype of HCV species present in the test sample, wherein if an HCV species of any one of HCV genotypes 1, 2, 3, 4, 5 or 6 is present in the test sample then the method amplifies a portion of the NS5b region and generates a nucleotide sequence of at least a portion of the NS5b region from said HCV species.

2. The method of claim 1, wherein the mixture of degenerate oligonucleotide PCR primers comprises degenerate oligonucleotide sequences defined by the following formulas:

SEQ ID NO: 7
    5'-TGG GGT TCK CGT ATG AYA CCC GCT G-3'

SEQ ID NO: 8
    5'-TGG GGT TCK CIT ATG AYA CYM GIT G-3';
    and

SEQ ID NO: 9
    5'-GAR TAY CTV GTC ATR GCI TCY GTR AA-3'.

3. The method of claim 1, wherein a portion of the NS5b region of at least one HCV species of genotype 6 is amplified.

4. The method of claim 1, wherein the amplifying is performed with a mixture of degenerate oligonucleotide PCR primers comprising each degenerate primer according to SEQ ID NO: 6 and SEQ ID NO:9.

5. The method of claim 1, wherein the generating is performed with a mixture of degenerate oligonucleotide sequencing primers comprising each degenerate primer according to SEQ ID NO: 1 and SEQ ID NO: 2.

6. The method of claim 4, wherein the generating is performed with a mixture of degenerate oligonucleotide sequencing primers comprising each degenerate primer according to SEQ ID NO: 1 and SEQ ID NO: 2.

* * * * *

SEQUENCE LISTING

<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
tatgayaccc gctgyttyga ytc                                          23

<210> SEQ ID NO 2
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (10)..(10)
<223> OTHER INFORMATION: n is i

<400> SEQUENCE: 2
vgtcatrgcn tcygtraagg ctc                                          23

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
tggggttckc gtatgayacc cgctg                                        25

<210> SEQ ID NO 4
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (11)..(11)
<223> OTHER INFORMATION: n is i
<220> FEATURE:
<221> NAME/KEY: misc_feature
<222> LOCATION: (23)..(23)
<223> OTHER INFORMATION: n is i

<400> SEQUENCE: 4
tggggttckc ntatgayacy mgntg                                        25

<210> SEQ ID NO 5
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (11)..(11)
<223> OTHER INFORMATION: n is i
<220> FEATURE:
<221> NAME/KEY: misc_feature
<222> LOCATION: (23)..(23)
<223> OTHER INFORMATION: n is i -continued

```
<400> SEQUENCE: 5
tggggttckc ntatgayacy mgntg                                            25

<210> SEQ ID NO 6
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 6
tggsbttykc ntaygayacy mgntg                                            25

<210> SEQ ID NO 7
<211> LENGTH: 25
<212> TYPE: DNA
<213> ORGANISM: Artificial Sequence
<220> FEATURE:
<223> OTHER INFORMATION: forward primer

<400> SEQUENCE: 7
tggggttckc gtatgayacc cgctg                                            25

<210> SEQ ID NO 8
<211> LENGTH: 25
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (11)..(11)
<223> OTHER INFORMATION: n is i
<220> FEATURE:
<221> NAME/KEY: misc_feature
<222> LOCATION: (23)..(23)
<223> OTHER INFORMATION: n is i

<400> SEQUENCE: 8
tggggttckc ntatgayacy mgntg                                            25

<210> SEQ ID NO 9
<211> LENGTH: 26
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: (18)..(18)
<223> OTHER INFORMATION: n is i

<400> SEQUENCE: 9
gartayctvg tcatrgcntc ygtraa                                           26

<210> SEQ ID NO 10
<211> LENGTH: 23
<212> TYPE: DNA
<213> ORGANISM: Artificial Sequence
<220> FEATURE:
<223> OTHER INFORMATION: forward primer
```

```
<400> SEQUENCE: 10
tatgayaccc gctgyttyga ytc                                              23

<210> SEQ ID NO 11
<211> LENGTH: 23
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: (10)..(10)
<223> OTHER INFORMATION: n is i

<400> SEQUENCE: 11
vgtcatrgcn tcygtraagg ctc                                              23

<210> SEQ ID NO 12
<211> LENGTH: 1944
<212> TYPE: DNA
<213> ORGANISM: Homo sapiens

<400> SEQUENCE: 12
cccgactccg acgttgagtc ctattcttcc atgccccccc tggaggggga gcctggggat       60
ccggatctca gcgacgggtc atggtcgacg gtcagtagtg gggccgacac ggaagatgtc      120
gtgtgctgct caatgtctta ttcctggaca ggcgcactcg tcacccgtg cgctgcggag       180 gaacaaaaac tgcccatcaa cgcactgagc aactcgttgc tacgccatca caatctggtg     240
tattccacca cttcacgcag tgcttgccaa aggaagaaga agtcacatt tgacagactg      300 caagttctgg acagccatta ccaggacgtg ctcaaggagg tcaaagcagc ggcgtcaaaa     360
gtgaaggcta acttgctatc cgtagaggaa gcttgcagcc tggcgccccc acattcagcc    420
aaatccaagt ttggctatgg ggcaaaagac gtccgttgcc atgccagaaa ggccgtagcc     480
cacatcaact ccgtgtggaa agaccttctg gaagacagtg taacaccaat agacactacc    540
atcatggcca agaacgaggt tttctgcgtt cagcctgaga aggggggtcg taagccagct    600
cgtctcatcg tgttccccga cctgggcgtg cgcgtgtgcg agaagatggc cctgtacgac     660
gtggttagca agctcccctt ggccgtgatg ggaagctcct acggattcca atactcacca     720
ggacagcggg ttgaattcct cgtgcaagcg tggaagtcca agaagacccc gatgggctc     780 tcgtatgata cccgctgttt tgactccaca gtcactgaga gcgacatccg tacggaggag     840
gcaatttacc aatgttgtga cctggacccc caagcccgcg tggccatcaa gtccctcact     900
gagaggcttt atgttggggg ccctcttact aattcaaggg gggaaaactg cggctaccgc     960
aggtgccgcg cgagcagagt actgacaact agctgtggta acaccctcac tcgctacatc    1020
aaggcccggg cagcctgtcg agccgcaggg ctccaggact gcaccatgct cgtgtgtggc    1080
gacgacttag tcgttatctg tgaaagtgcg ggggtccagg aggacgcggc gagcctgaga    1140
gccttcacgg aggctatgac caggtactcc gcccccccg ggaccccccc acaaccagaa     1200
tacgacttgg agcttataac atcatgctcc tccaacgtgt cagtcgccca cgacggcgct    1260
ggaaagaggg tctactacct tacccgtgac cctacaaccc cctcgcgag agccgcgtgg     1320 gagacagcaa gacacactcc agtcaattcc tggctaggca acataatcat gtttgccccc    1380
acactgtggg cgaggatgat actgatgacc cacttcttta gcgtcctcat agccagggat    1440
cagcttgaac aggctctcaa ctgcgagatc tacgagcct gctactccat agaaccactg     1500
gatctacctc caatcattca aagactccat ggcctcagcg cattttcact ccacagttac    1560
```

```
tctccaggtg aaattaatag ggtggccgca tgcctcagaa aacttggggt cccgcccttg    1620
cgagcttgga gacaccgggc ctggagcgtc cgcgctaggc ttctggccag aggaggcaag    1680
gctgccatat gtggcaagta cctcttcaac tgggcagtaa gaacaaagct caaactcact    1740
ccgataacgg ccgctggccg gctggacttg tccggctggt tcacggctgg ctacagcggg    1800
ggagacattt atcacagcgt gtctcatgcc cggccccgct ggttctggtt ttgcctactc    1860
ctgcttgctg caggggtagg catctacctc ctccccaacc gatgaagatt gggctaacca    1920
ctccaggcca ataggccatt ccct                                           1944
```